United States Patent
Nath

(10) Patent No.: US 12,347,571 B2
(45) Date of Patent: Jul. 1, 2025

(54) DIGITAL PROFESSIONAL BUSINESS CARD AND COMMUNICATION SYSTEM

(71) Applicant: Tellus Medical Solutions LLC, Setauket, NY (US)

(72) Inventor: Badri P. Nath, Setauket, NY (US)

(73) Assignee: Tellus Medical Solutions LLC, Setauket, NY (US)

( * ) Notice: Subject to any disclaimer, the term of this patent is extended or adjusted under 35 U.S.C. 154(b) by 0 days.

(21) Appl. No.: 18/366,799

(22) Filed: Aug. 8, 2023

(65) Prior Publication Data

US 2023/0386683 A1    Nov. 30, 2023

Related U.S. Application Data

(63) Continuation of application No. 16/570,683, filed on Sep. 13, 2019, now Pat. No. 11,721,442.

(60) Provisional application No. 62/731,187, filed on Sep. 14, 2018.

(51) Int. Cl.
| | | |
|---|---|---|
| *G16H 80/00* | (2018.01) | |
| *G06F 3/04817* | (2022.01) | |
| *H04L 51/063* | (2022.01) | |
| *H04L 51/52* | (2022.01) | |
| *H04W 4/14* | (2009.01) | |

(52) U.S. Cl.
CPC .......... *G16H 80/00* (2018.01); *G06F 3/04817* (2013.01); *H04L 51/063* (2013.01); *H04L 51/52* (2022.05); *H04W 4/14* (2013.01)

(58) Field of Classification Search
CPC ........ H04L 51/063; H04L 51/52; H04W 4/14; G06F 3/04817; G16H 80/00
See application file for complete search history.

(56) References Cited

U.S. PATENT DOCUMENTS

| | | | | |
|---|---|---|---|---|
| 8,874,148 | B2* | 10/2014 | Herz | H04L 51/58 455/466 |
| 2011/0113084 | A1* | 5/2011 | Ramnani | H04W 4/16 709/201 |
| 2015/0379471 | A1* | 12/2015 | Lee | G06Q 10/10 705/342 |
| 2017/0364481 | A1* | 12/2017 | Scapa | H04L 51/48 |
| 2019/0182299 | A1* | 6/2019 | O'Brien | H04L 65/4015 |

\* cited by examiner

*Primary Examiner* — Jungwon Chang
(74) *Attorney, Agent, or Firm* — Squire Patent Consulting; Brendan E. Squire

(57) ABSTRACT

A system, method and apparatus for a Digital Professional Business Card. The digital professional business card provides a better way of communication between healthcare providers and patients. With digital application communication through a smart phone, there are no more lost business cards, forgotten verbal communication. Establishing contact is instantaneous and requires minimum number of steps. In addition, it provides a for expanded two way secure communication platform.

20 Claims, 13 Drawing Sheets

To send a message to a patient, The medical professional shares their digital business card The patient, opens the Tellus or receives an SMS invitation to download the application The physician can then create a direct message with the patient or add them to a group chat

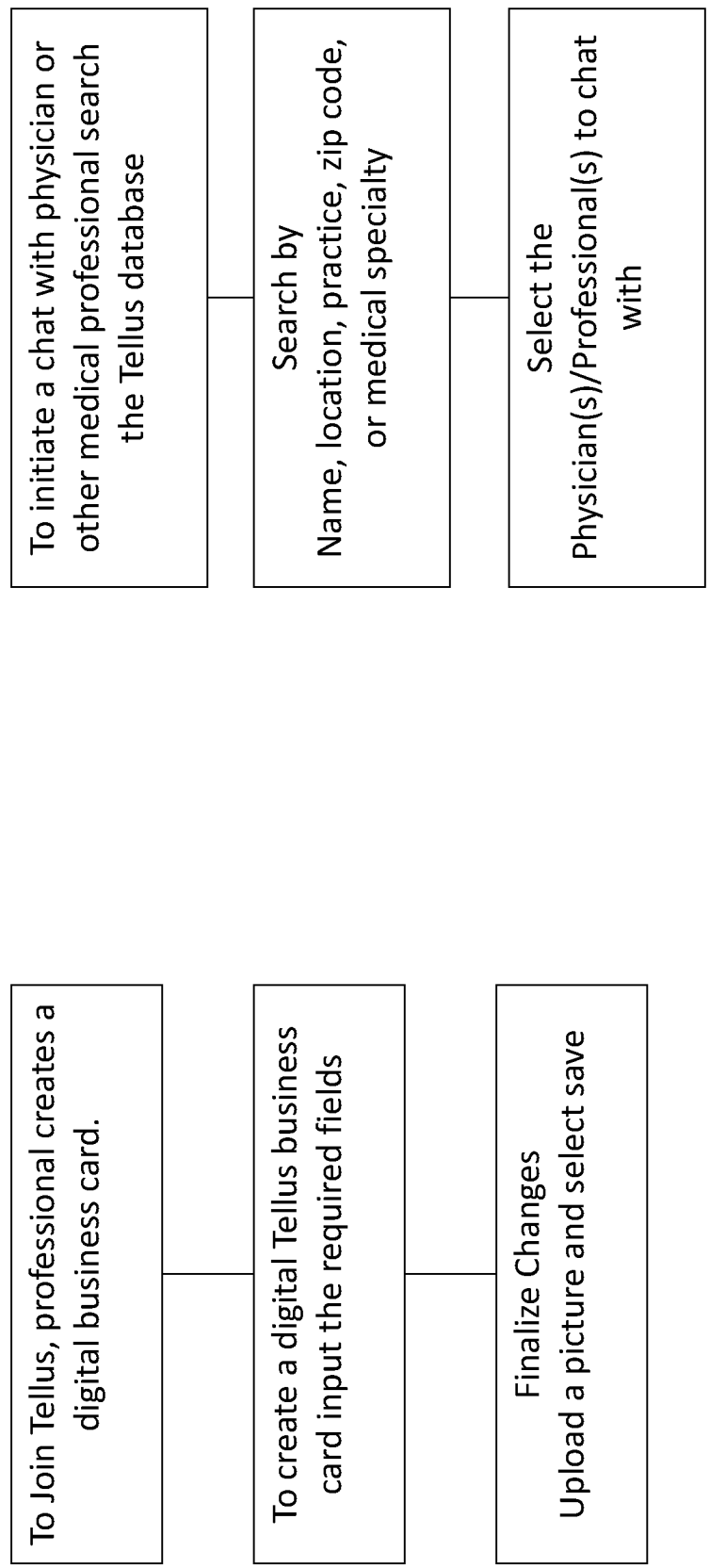

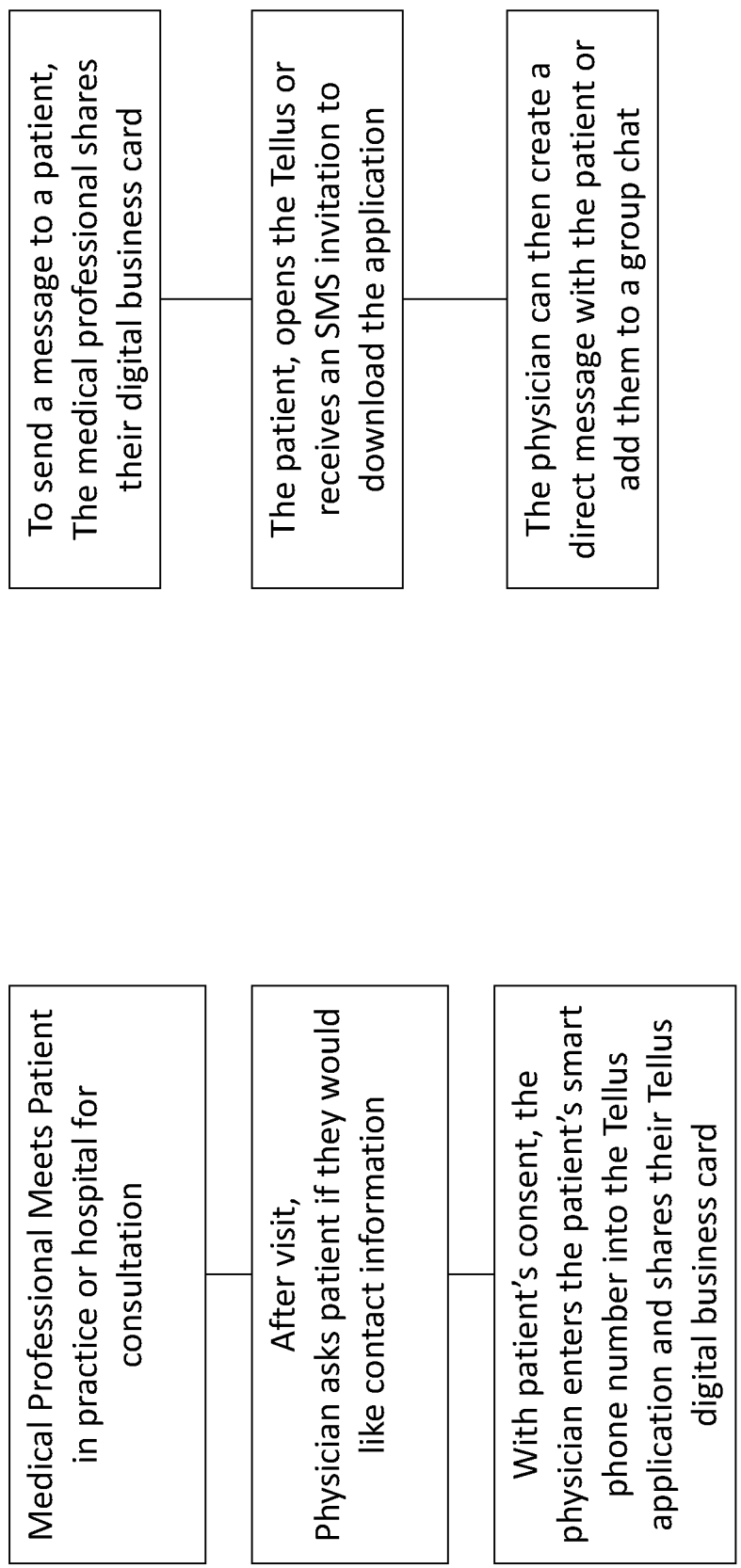

DIGITAL PROFESSIONAL BUSINESS CARD AND COMMUNICATION SYSTEM

CROSS-REFERENCE TO RELATED APPLICATION

This application is a continuation of U.S. patent application Ser. No. 16/570,683, filed Sep. 13, 2019, and claims the benefit of priority of U.S. provisional application No. 62/731,187, filed Sep. 14, 2018, the contents of which are herein incorporated by reference.

BACKGROUND OF THE INVENTION

The present invention relates to the exchange of contact, and other business information, and more particularly to the exchange of information via a digital business card.

Current paper-based business cards can get lost, do not provide continued interaction in a fast paced environment, and they are not two way form of communication. Paper business card is also limited by its passive nature of communication. Although the current paper-based card drawback applies all aspects of business, it is acutely felt in industries like healthcare. For example: Currently, there is serious communication gap between patients and health care providers. When patients are admitted to hospitals, they are seen by multitude of specialists. It is nearly impossible for patients and their relatives to keep track of names and contact information of the specialists.

Old-fashioned, traditional paper business cards are lost or misplaced frequently. In healthcare, it results in lack of communication between patient and the healthcare providers. Lack of communication results in dissatisfaction and potential medico-legal adverse actions. In addition, communication is often fragmented with many key players in the line of treatment often being kept out of the loop resulting in a serious communication gap between patients and health care providers.

When patients are admitted to hospitals, they are seen by multitude of specialists. It is nearly impossible for patients and their relatives to keep track of names and contact information of the specialists. They require many more steps to execute the desired outcome, which are cumbersome in the world of fast paced business environment. The drawbacks cited in healthcare industry can also be seen in many other industries using paper business card and so generalized. Alternative methods of communication, especially within healthcare, include traditional text and SMS messaging and e-mail exchange.

Existing methods of creating digital business cards do not allow users to share these cards with desired recipients easily or create customize cards with pictures for easy identification. Likewise, while other professional websites can include professional marketplaces/domains, which do not list business contact information and instead only provides the online resumes of users.

Within healthcare, communication through these alternatives and existing means is not HIPAA compliant/secure and as a result is often fragmented. Personal and private messages are also mixed. More specifically, personal messaging applications are often used for both work and private usage.

Furthermore, users are unable to maintain control and anonymity of their private contact information or cell phone number in these exchanges of information. Alternative methods also do not allow professionals to search for others within a centralized database to easily contact, message and communicate with them, without exchanging personal cell phone numbers. Existing, alternative methods of communication between medical professionals and patients often do not ensure physician verification or encrypted message communication.

As such, there is an immense need for improved communication in a professional and personal setting.

SUMMARY OF THE INVENTION

In one aspect of the present invention, a system for dissemination of a digital professional business card and communications between a professional and a client of the professional is disclosed. The system includes a server configured to communicate with one or more computing devices. A messaging framework provides electronic communications between the one or more computing devices and a program product comprising machine-readable program code for causing, when executed, the server to perform process steps. The process steps include receiving identification information for the professional for dissemination as the digital professional business card. A phone number corresponding to the client is received from a first mobile computing device of the professional. The identification information for the professional is transmitted to a second mobile computing device of the client as an SMS message. The SMS message contains a link to access an application for interacting with the server.

The identification information includes a name, an occupation, a contact address, a phone number, and an image of the professional.

In other embodiments, responsive to an instruction received from the client, the application is delivered to the second mobile computing device. The system provides communications functionality between the first mobile computing device and the second computing device. The communications functionality includes a chat messaging system.

In some embodiments, the chat messaging system receives a designation of a chat group from the first computing device. The chat group may include the professional, a team of professionals, and the client. In certain embodiments, the chat messaging system receives an instruction from the first computing device to exclude the client from communications within the chat group.

In other embodiments, information corresponding to each member of the team of professionals is delivered to the second mobile computing device.

The system may also be configured to receive a designation of a client proxy from the second computing device. When designated, chat group messages are delivered to a computing device of the client proxy.

The system may also be configured to receive an instruction to preserve chat messages in a conversation from one or more of the first computing device and the second computing device and store the chat messages in the conversation.

In preferred embodiments, the professional is a physician and the client is a patient.

Other aspects of the invention include a computer program product stored on a non-transitory computer storage medium comprising machine readable program code for causing, when executed, a computing device to perform process steps. The process steps include accessing a system, hosted on a server, for the dissemination of a digital professional business card and a communication between a professional and a client with a login credential associated with the user.

A digital professional business card is presented in a display of the computing device. The digital professional business card corresponds to a professional associated with the computing device. An input field is presented to receive a name and a phone number of a client in the display of the first computing device with the digital professional business card. A send button is presented in the display of the first computing device with the digital professional business card.

In some embodiments, an input of the name and phone number of the client is received in the input field. An invitation comprising a V-card representation of the digital professional business card is transmitted to the client via an SMS message upon activation of the send button, the SMS message containing a link to access the computer program product.

In yet other embodiments, a menu is presented in the display. The menu provides a first control to initiate a chat messaging conversation and a second control designating a group to participate in a group chat messaging conversation.

In other embodiments, a list of one or more conversations is presented in the display. The list has a group icon for each of the one or more conversations corresponding to a group chat messaging conversation. An indicator on the group icon is provided for designating the group as restricting communication of the group chat messaging conversation with the client.

In other embodiments, an indicator on the group icon shows that the chat messaging conversation is designated for preservation.

In other embodiments, a conversation window displays one or more chat communications for the group chat messaging conversation. A representation of the group icon is presented in the conversation window.

A conversation window displaying one or more chat communications for the group chat messaging conversation is presented. A representation of the group icon in the conversation window is also displayed. When the group chat messaging conversation is designated as restricted, a share control is presented after each of the one or more chat communications in the group chat messaging conversation. The chat communication may be shared with the client upon activation of the share control corresponding to the one or more chat communications in the group chat messaging conversation.

In yet other aspects of the invention, a computer program product stored on a non-transitory computer storage medium comprising machine readable program code for causing, when executed, a computing device to perform process steps. The process steps include accessing a system, hosted on a server, for the dissemination of a digital professional business card and a communication between a professional and a client with a login credential associated with the user. A digital professional business card is presented in a display of a computing device. The digital professional business card corresponds to a professional. A conversation list is presented in the display of with the digital professional business card.

In other embodiments, the steps include presenting a conversation window displaying one or more chat communications corresponding to a selected chat messaging conversation from the conversation list. A menu selection may be presented in the conversation window, the menu including a conversation preservation control where the selected chat messaging conversation is responsive to a selection of the conversation preservation control.

In yet other embodiments, the steps include presenting a menu selection in the conversation window. The menu includes an invite proxy control. An input designating a proxy may then be received. When the proxy is not associated with the system, an invitation comprising a V-card representation of the user is transmitted to the proxy via an SMS message, the SMS message containing a link to access the computer program product. When the proxy is associated with the system, the proxy is joined to the selected chat messaging conversation.

In another embodiment, a menu selection is presented in the conversation window, the menu including a report user control. A report about the professional may be received upon activation of the report user control.

In another embodiment, when the selected chat conversation is a group chat conversation, the digital professional business card for one or more other professionals in the group chat conversation is received by the user.

These and other features, aspects and advantages of the present invention will become better understood with reference to the following drawings, description and claims.

BRIEF DESCRIPTION OF THE DRAWINGS

FIG. 12 is a flow chart for steps for preparing a digital professional business card.

FIG. 13 is a flow chart for locating a physician within the digital professional business card system.

FIG. 14 is a flow chart for initiating a physician contact with the patient through the digital professional business card system.

FIG. 15 is a flow chart for a physician to invite a patient to participate in the digital professional business card system.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention provide a system method and apparatus for the exchange of a digital business card. As stated above, current paper-based business cards can get lost, do not provide continued interaction among the parties involved in a fast-paced environment, and they are not two way forms of communication. Paper business card are also limited by their passive nature of communication. Although the current paper-based card drawback applies across all aspects of business, it is more acutely felt in industries like healthcare.

With the present invention, establishing contact is instantaneous, requires minimum number of steps, and protects privacy (especially of the sender as their personal smartphone number is kept private). In addition, it establishes the basis for an expanded two-way secure communication platform. The application allows for the formation of group chats and allows for the electronic transfer of digital business cards.

The present invention digitizes and centralizes the way we communicate and share information with each other. Users can download, store and organize existing digital business cards they have received within their interface and their portal and save these cards with them forever. The system of the present invention allows for the exchange of digital business cards through a cellular application with the sender's personal number remaining private. Users can share the business cards of colleagues as well through the application with other participants.

Within healthcare, the application allows for direct and group messaging between various industry stakeholders (physician to physician, physician to patient) and allows users to search for other members in a centralized database with specific search queries. As such, knowing the personal and private cell phone number of key players within the industry is not needed. In this way, different members can communicate through the application without all parties knowing the personal cell phone number of different members.

Figure 5:
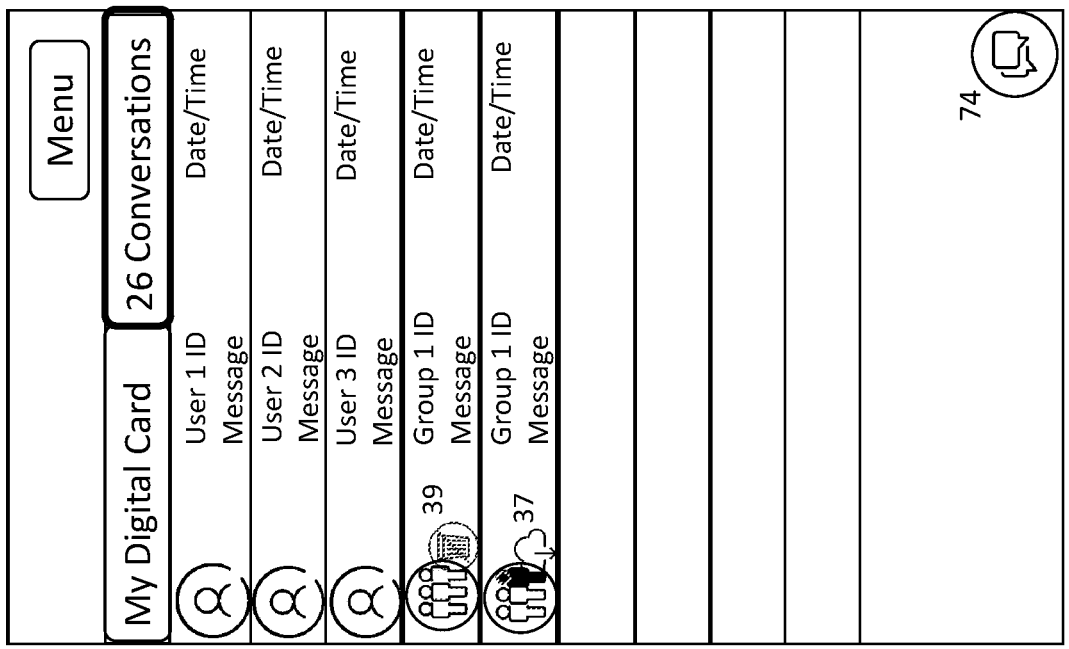
FIG. 5 is a representative screen capture of a conversation for the digital professional business card communication system with an attached file icon.
Figure 4:
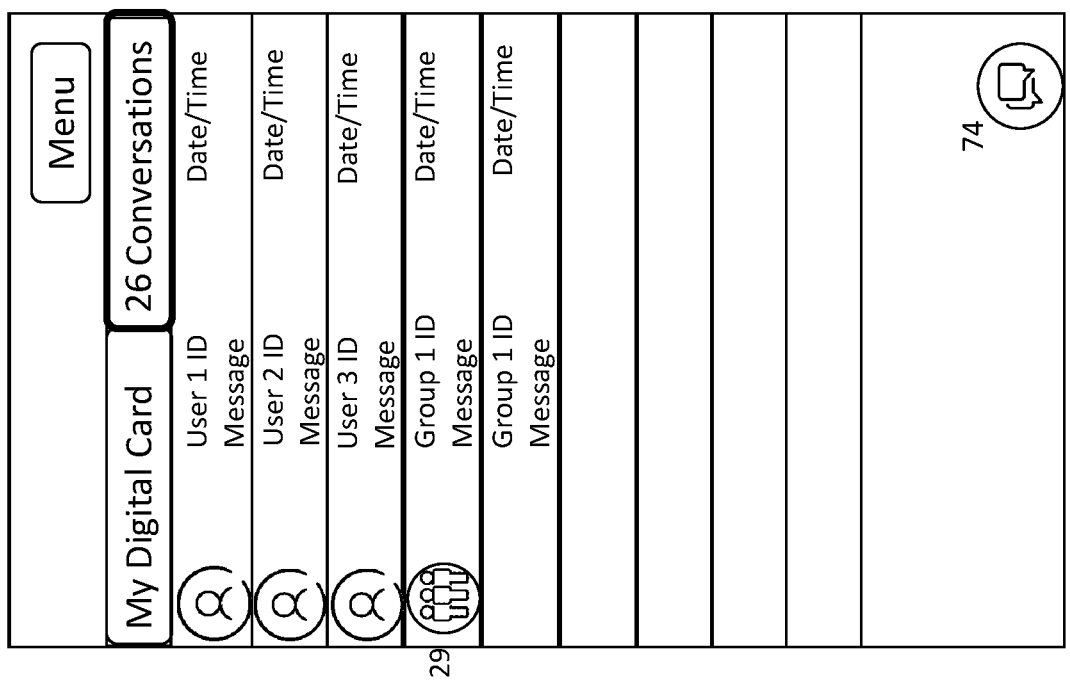
FIG. 4 is a representative screen capture of a conversation for the digital professional business card communication system on a physician screen with an open conversation icon, a preserved conversation icon, and a restricted conversation icon.

The system of the present invention presides of the centralized messaging between different stakeholders within the healthcare system and is not limited to text messaging, but also includes the transmission/exchange of images, pictures, charts, videos, links, and other attachments. Which may be indicated with an attachment icon 37, shown in FIG. 5. Likewise, the system is not limited to a telephone application and also includes communication via computer (program, application or website).

This application also provides patient communication to include a healthcare proxy or next of kin designated by the patient. Once authorized, relatives and friends of the patient with a smart phone may be entered into the application as a healthcare proxy or next of kin such that information that the patient receives about their care is automatically exchanged with them as well. The system also provides integration of email communication from patients to administrators via the message channel. Any messages sent to the physician from the patient or healthcare proxy are automatically curated into an appropriate format and sent to the email provided on the professional's business card.

Figure 1:
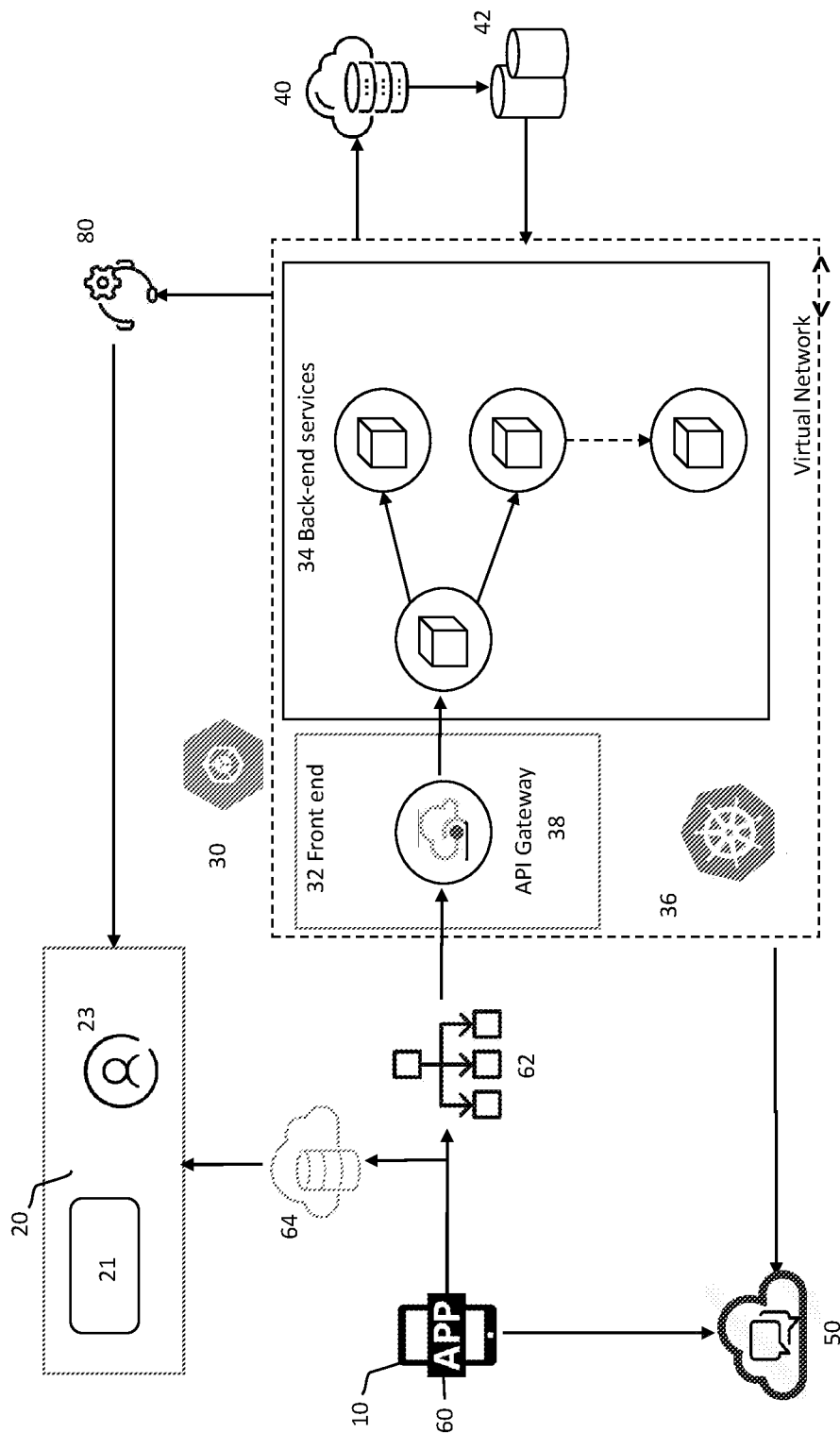
FIG. 1 is a system architecture for an implementation of the digital professional business card and communication system.

As seen in reference to FIG. 1, a digital professional business card system according to the present invention is a hybrid application using an ionic framework. The application allows for the exchange of information between various parties and allows the creation of digital business cards 20, which can be shared with other users. Within healthcare sector, the application 60 may also provide forms for registering practice administrators, physicians and patients. The system includes a containerized application management system 30, such as Google's Kubernetes Engine (GKE), that provides front end 32 and back-end services 34 for the application. A container-orchestration system 36 provides for automating deployment, scaling and management of containerized application 60. The services are accessed via an API gateway 38.

The application 60 is based upon a NO SQL database platform 40 hosted on a cloud service, such Google Cloud Datastore, provides for automatic scaling, high performance, and ease of application development. The application 60 may access the system via a load balancer 62. A cloud storage 64 is provided to house the application 60 for distribution.

The messaging framework 50 may be built using a cloud communications platform as a service (CPaaS), such as Twilio, which will enable users to initiate one on one or group chats. The chat functionality is provided in real time and it also provides additional communications functionality, including e-mail and telephonic communications.

Users of the system are provided functionality through a graphical user interface (GUI) of the application 60 based on one or more roles and permissions. The one or more roles include a Super Admin; a Physician; a Practice Admin; a Patient; a Healthcare Proxy/Next of Kin;

Super Admin

A super admin, is provided permissions to activate/deactivate a physician/staff member. As soon as the super admin logins to the app, they are presented Super Admin home page. On the Super Admin Home page, the Super Admin is presented two options All Physicians and Subscribed Practices, which permits viewing and editing of parameters for subscribed practices and all practice members.

When the super admin clicks All Physician button, they are navigated to a page where they can search for a physician. As soon as Super Admin types in at least two characters in a search box, the search result should begin to appear as list. The Super Admin can then click on any of the physician, staff or other user, and open the physician detail page. On the physician detail page, the Super admin is able to change a status from Activate and Deactivate and vice versa.

As soon as the active status is updated to deactivated, the physician's profile is deactivated. If the deactivated user is trying to login to the app, they will be presented an error message indicating that their account is locked out, please contact support. In the case the user is logged in, they may be automatically redirected to a new page which will display the message indication that their account has been disabled. And asking them to contact the admin.

If the physician has been disabled by the Super Admin, that physician will also be deactivated from the practice. If an invited physician has been deactivated and reactivated, the physician will be associated with the same practice.

When the super admin clicks on "Subscribed Practices" button, they are navigated to a page where they can see the list of subscribed practices. As soon as the super admin opens any of the practices, they may be presented a field for subscription count (along with other practice details). To edit the subscription counter for physician/clinician and support staff of the practice. The Super Admin may be able to increase the subscription count using that field. As soon as the super admin clicks on a Save button, the subscription count for the subscribed practice is updated. Once the subscription count is updated, one confirmation should be displayed to the user on the toast. After a successful update, the super admin will be navigated back to the practice list screen.

Figure 3:
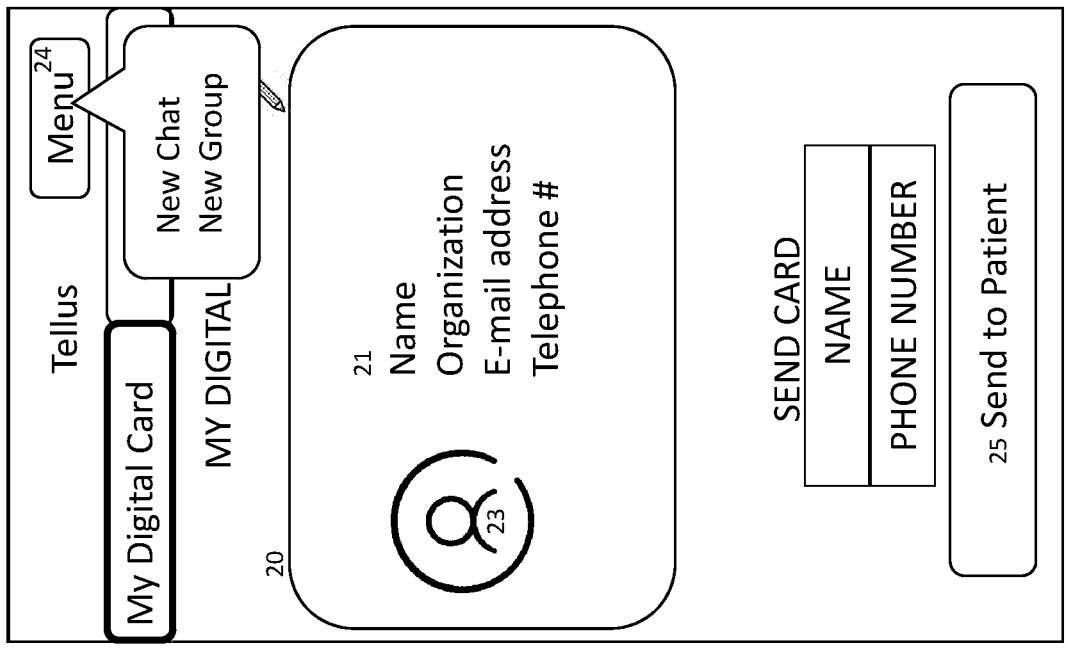
FIG. 3 is a representative screen capture of a menu selection for the digital professional business card on a physician screen.
Figure 2:
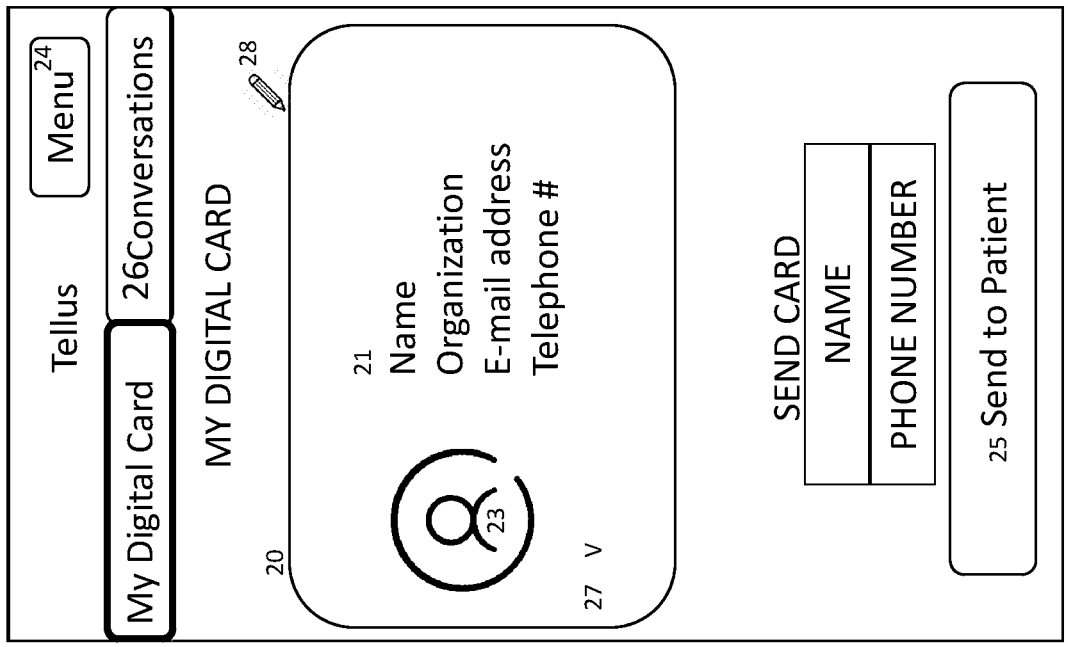
FIG. 2 is a representative screen capture for a digital professional business card on a physician screen.

A Physician is able to login to the app 60 using OTP verification, the physician is presented the physician home page, such as shown in reference to FIGS. 2-3, with their digital business cards 20. On successful Mobile Verification, the Physician is presented their own Home Page. The Physician home page has three tab sections: a My Digital Card 22, a Groups 24 and a Conversations 26.

The 'My Digital Card' section provides an editable Physician's digital business card 20. Physician digital business card 20 has a region 23 for his image, and a plurality of fields 21 including: name, practice name, contact umber and email id, such as shown in reference to FIGS. 2 and 3. A verified physicians may have a verified icon 27 next to their name on their digital business card 20.

An edit control 28 is provided to enable editing of the digital business card 20. When the edit control 28 activated, at the bottom, the physician is presented list of available templates for their profile. The physician is able to select any of the template and click on save button to reflect changes in the profile. Individual fields in the profile may be edited by selecting the desired field.

Once a save control is selected, the selected template and any changes to the profile fields are applied to the digital business card 20. The same template will be sent in an MMS when the physician invites any patient. If the physician has not selected any templates, then the default template will be shown. Once a Physician creates a digital professional business card 20, they are registered within the system and so other physicians can search for them to initiate chats.

A send control 25 is provided for the physician to share their digital business card 20. There is a numeric field to enter Patient's mobile number and a alphabetic field to enter the patient's name. A 'Send to Patient' button 25 transmits the digital business card 20 via the messaging framework 50 to invite the Patient designated.

Figure 10:
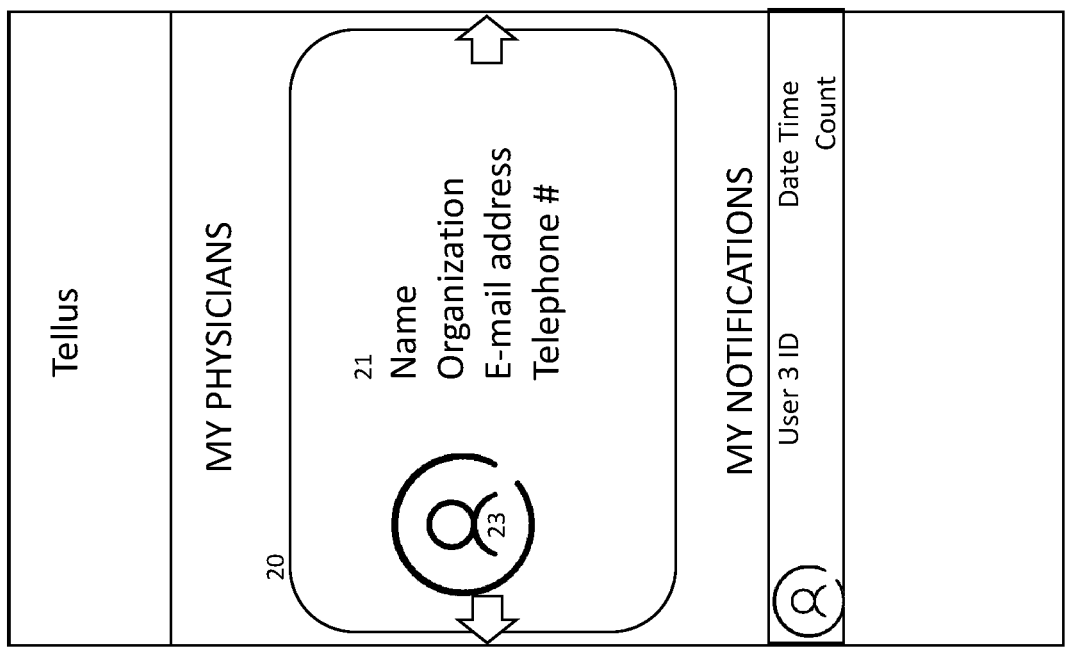
FIG. 10 is a representative screen capture of a digital professional business card on a patient screen.

As soon as the invitation is sent to the patient, the invite is available in the Conversation tab 26. As seen in reference to FIG. 14, the invitation is sent to Patient via SMS, and includes a link to the web app 60 to launch the app store 64 depending on the platform of the patient's mobile device. A v Card of the clinician is sent to the invited user mobile number. If the Invited Patient is first time app user, a text message will be sent to his number. If the Invited Patient is an existing app user, an app notification will be shown up to accept/cancel invite, as seen in reference to FIG. 10. The Physician will be presented with a confirmation message, such as "Your Digital Card has been sent" message after sending the invite with Continue button.

As seen in reference to FIG. 3, the physician can click on the invited patient channel, or menu button 24, or the conversation tab 26 and initiate a chat communication with the patient. The physician is also presented an option to specify a new group for the chat session, including the invited patient who has not completed OTP verification/not logged on to the system. The group may include other physicians and members of the patient's treatment team designated by the physician or a Practice Administrator. As soon as the user clicks on the New Group button, the user is presented a listing where they can see the list of all the physicians/PA in the system. The user can select multiple clinicians/physician and click on the Next button to initiate the group chat. As soon as the user clicks on a Next button, a pop-up should be opened to the user asking for group name where the Physician/PA will be able to add a name of the group. A group chat is indicated in the conversations interface by group icon 29. Selecting the group icon 29 will display a listing of the participants in the group.

Figure 7:
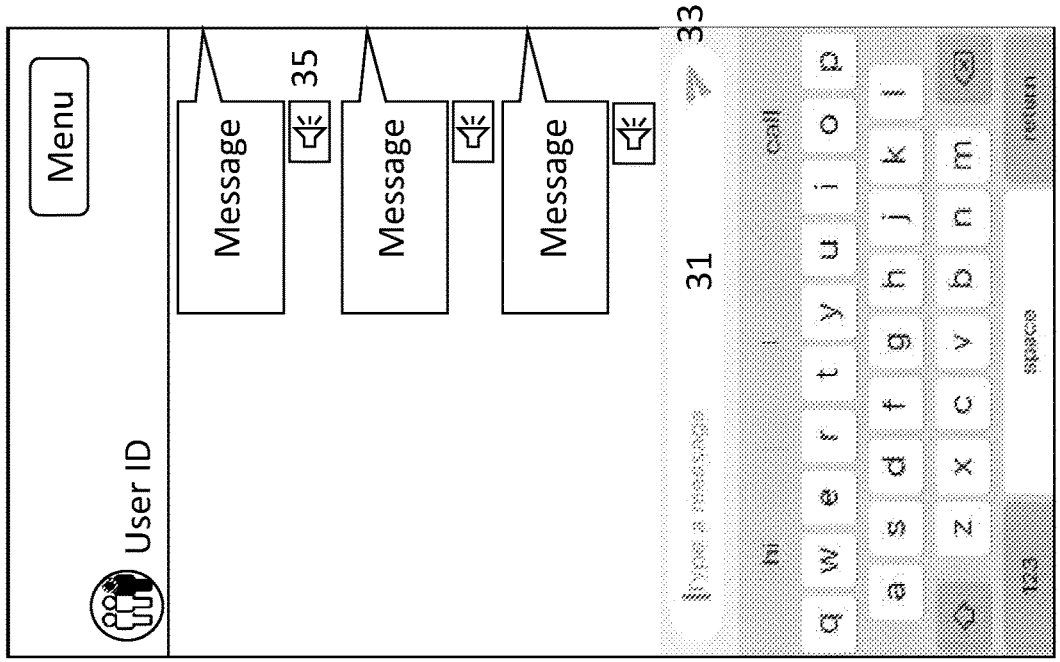
FIG. 7 is a representative screen capture for a messaging window.
Figure 9:
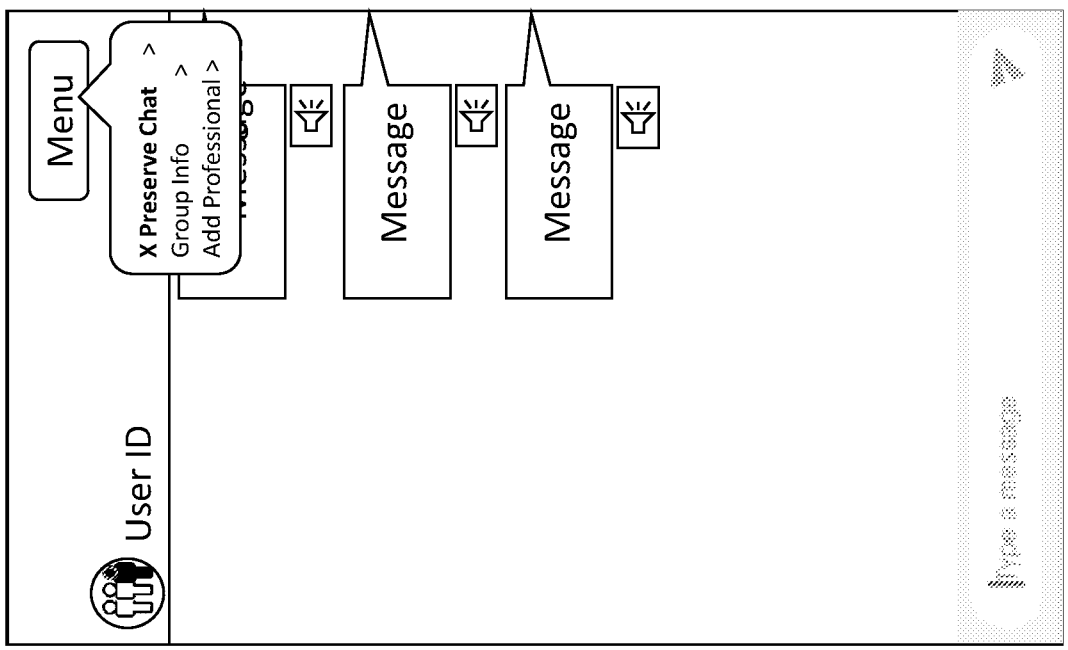
FIG. 9 is a representative screen capture showing a conversation menu for the digital professional business card communication system showing a preserve chat selection.
Figure 8:
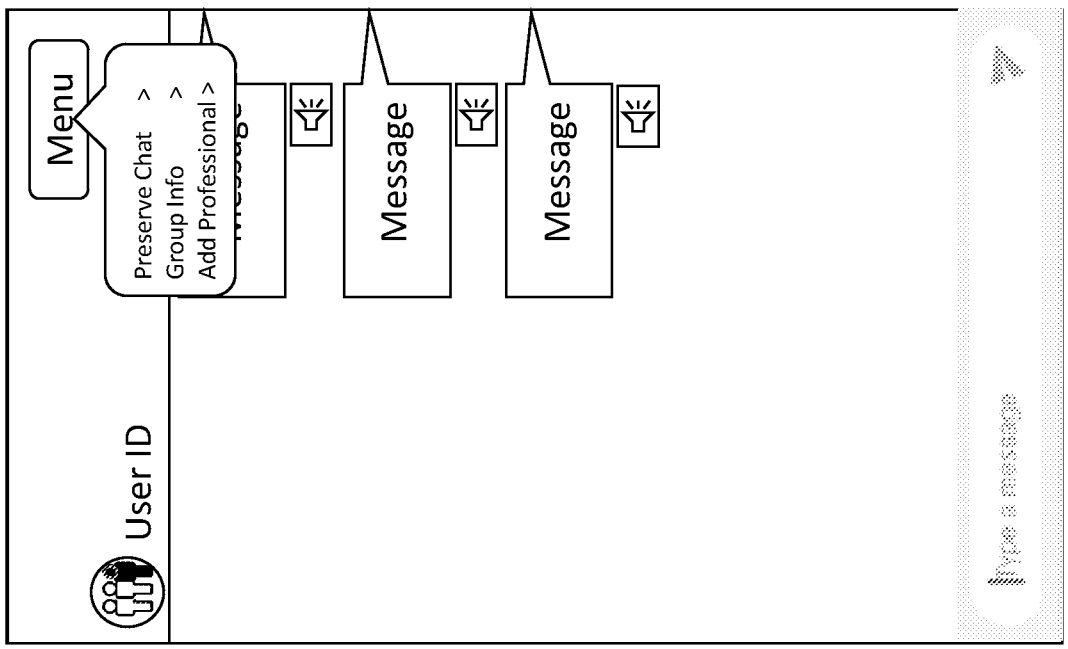
FIG. 8 is a representative screen capture showing a conversation menu for the digital professional business card communication system.

A physician may also be presented with a list of patients. The physician may select any of the patients from the patient list, a new page is opened, and a new chat window, such as shown in FIGS. 7-9, is presented with the name and an image of the patient, or group icon 29 may be displayed. The physician can send a message to the patient after typing it in the a text box 31 in the chat window. In some embodiments, a send button 33 is disabled until an entry is made in the text box. In the chat window, below each message that the physician has sent to patient, an orange horn icon 35 may be displayed indicating that the message has been sent to a patient. When the send button is activated, same message is sent to the patient and should also be displayed in the message window.

Selection of the conversations tab 26 opens a conversations interface that displays conversations that the physician is participating in. The conversations are presented chronologically, with a link to the profile of the other users participating in the conversation. As soon as the user clicks on an Ok button on the popup screen, the group chat should be initiated and it should open the group conversation in front of the user. A cancel button, may be provided to cancel the group conversation.

Through the physician GUI, the physician can also deliver messages to the patient. The messaging functionality is also configured so that the Patient should not get messages unless the physician wants to include the patient in the conversation, such as to consult independently with another physician or member of the care team before discussing with the patient. In this case, the group icon 29, is presented with an indicator, such as a different color or shaded group member to indicate the group is restricted. The physician can send a message to the patient by clicking on a Horn button 35 on the chat conversation page. As soon as the Horn button is clicked, the physician may confirm whether they want to deliver the message to patient or not. As soon as the clinician selects YES, the message is delivered to the patient. If the clinician selects No, then the message will not be delivered to the patient. Also the physician can select on a check box control below the prompt message to opt if they don't want a confirmation message.

In addition, on the physician's list page, the physician can click on any of the participating physicians to initiate a chat. In case if the list is empty, there are no physicians included in the group, the physician can click on an Add button on the Clinician group to open the list of physicians and select any of the physician from there. When the physician clicks on any of the clinician list item, they are navigated to physician chat page. Once the physician is done with chatting and they click on a back button, or enter a gesture, and they are navigated back to clinicians group page. On the clinician group page, the latest communication is reflected.

Typically inactive message channels are automatically delete after a period of 14 days, or other predetermined temporal period of inactivity. The individual message channel's may also have a menu option, such as show in reference to FIG. 9, settings can also be selected such that the chat is preserved so that it is saved until it is deleted. An icon 39 may be added to the group icon 29 to indicate that the conversation is set for preservation.

When a physician opens the Groups\-\→Patient Groups section, a list of invited patient should be displayed. On the list, if the patient invitation is pending, then the status Pending is displayed in front of the patient in the field where the time and counter is displayed. If the physician has communicated with the patient then it displays the last communication time and status. The status for the last sent message can be single tick grey, double tick grey, double tick blue, or other visually distinguishing element.

Patient

A patient can login to a patient home page. A representative patient home page is shown in reference to FIG. 10. An existing patient receive a push notification when physician sends a message. On the patient home page, in my notifications section, the patient can see all the messages which were sent to them. The notification has the image of the physician, name of the physician and the specialty. The notification may also indicate the number of unread messages. If the notification is from a verified physician then the profile may have the verified icon 27.

As indicated previously, when the physician sends an invite to an existing patient in the system, a push notification is sent to the patient. If the patient is a first time user, a SMS for vCard id also be sent to the patient. The patient receives a push notification with the text You've been invited to use Tellus® App by {name}. Clicking on the notification downloads opens the app 60 for the user. As soon as the patient logins to the app, they can start receiving messages (using the horn icon) which were sent after the patient logged in and presented the patient home page, where they are presented the physician's card 20 on the patient home screen.

In the patient and physician chat window, the patient is presented a mail button 74 with mail icon. When the patient selects the mail icon 74, then they are navigated to a new screen where they will be able to compose a new e-mail and send it to the physician. On the mail compose page, the patient should be able to see To, From, Subject Message fields. The To field and from field can be auto populated with the email address of the physician and the patient respectively. Typically the To and From fields are be read only, to prevent inadvertent alteration of the addresses. The patient will be able to send the email by clicking a send button in the compose e-mail window. The patient has the ability to go back to the physician chat window by using a back button.

Once the patient clicks on the send button, the mail is sent to the client and patient is navigated to the chat window. Also a toast should indicate that the email was sent successfully to the physician. In case there is any error while sending the email, it is displayed in the toast right below title of the physician.

Figure 11:
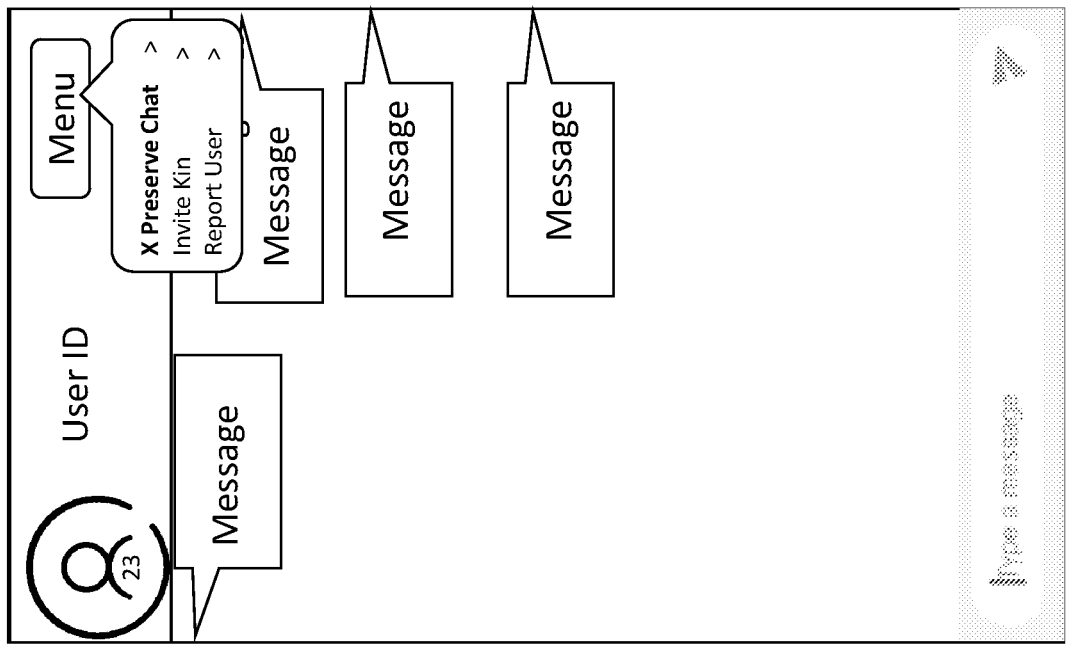
FIG. 11 is a representative screen capture of a digital professional business card on a patient screen showing a patient selection menu.

In other aspects of the invention, such as shown in reference to FIG. 11, a Patient, can nominate a healthcare proxy/next of kin to be part of messaging with the Physician. In the Patient home screen, the patient can add kin to be part of conversation by clicking 'Invite a Kin' in menu selection icon. Clicking on it will open a page where the user can enter the mobile number of healthcare proxy/next of kin and also see a consent form. The user can accept the consent and click on Continue button to proceed. As soon as the user clicks on the Continue button, they will be navigated to a page which will indicate Invitation successful, similar in operation to that described previously for the patient. Clicking on Continue button on the confirmation page will navigate the user back to the chat window.

A patient chat window may also include an Exit Group menu option. Once the patient selects the Exit Group button, a confirmation pop up should be displayed to the patient in a two button YES and NO format:

*Do you want to exit the conversation?*

If the patient chose Yes then they should be exited from the chat. The patient should not be allowed to email to the clinician through that conversation after they exit. The patient should also not get any messages from the conversation after exiting.

The healthcare proxy and one or more designated next of kin receives message alert about invite from Patient with a URL link to download the app 60. The Kin will also receive the digital card of physician which are part of the conversation. The group icon 29 may be modified to indicate the presence of the proxy.

The patient can also provide consent to share data with Physician and Practice Administrators. Upon successful OTP authentication, if the patient is logging in in for the first time, then the patient may be navigated to a patient terms and condition page. The patient can accept the terms and condition by selecting a checkbox control. After accepting the terms and conditions, the patient is navigated to the patient home page.

Figure 6:
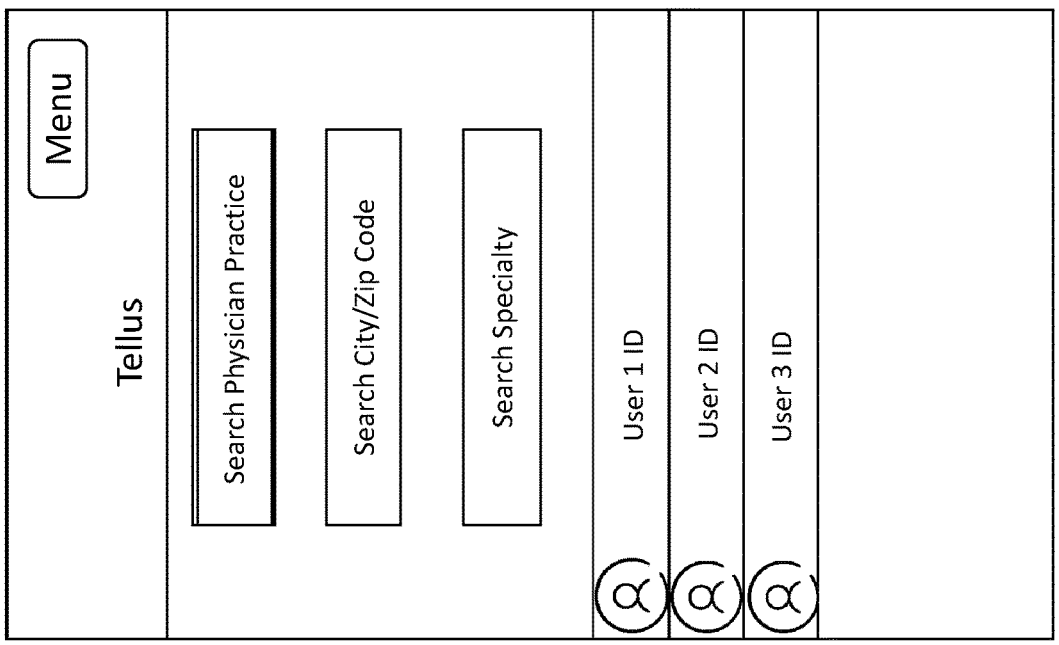
FIG. 6 is a representative screen capture for a search functionality for the digital professional business card communication system.

As seen in reference to FIG. 6, a patient may also be able to utilize the application 60 to search for most relevant physician based on my area code, and one or more filter criteria for specialty and Practice. In the search window, the patient has the ability to search for a physician based on various search criteria, such as the physician's name and other search criteria. Filter criteria is not mandatory and the results are preferably sorted based on my area code, or postal code.

Practice Administrator

A Practice Administrator, can use a code, so that the Practice Administrator can register the practice and start inviting clinicians in the practice. The Practice Administrator may also receive a subscription code. If the code is verified by the system, the registration page is shown where they can enter their details (similar to physician registration page). The admin contact number and email mentioned above should be configurable. The Practice Administrator who registers using the code will also be a verified user (verified user icon should be displayed).

The practice administrator may have privileges to establish profiles for one or more physicians in the practice. After creating the profile, an invite, similar to that sent to a patient is sent to the physician. Once the physician has downloaded the application 60, functionality of the physician's application 60 is as previously described. The practice administrator may also send out invitations to patients and other healthcare providers in the practice. The practice administrator may also request additional subscriptions or remove subscriptions based on the number of users in the practice.

Self Registered/Uninvited Users

While the previous discussion has indicated that new users may be added by an invitation process, with embedded links to the application, the system may also accept one or more Self Registered users. In this case, the user downloads the application 60 on their mobile device 10. Once the user is registered with the system, designating their particular role, patient or physician, the functionalities described previously are provided through a corresponding home page.

Database Architecture

Figure 21A:
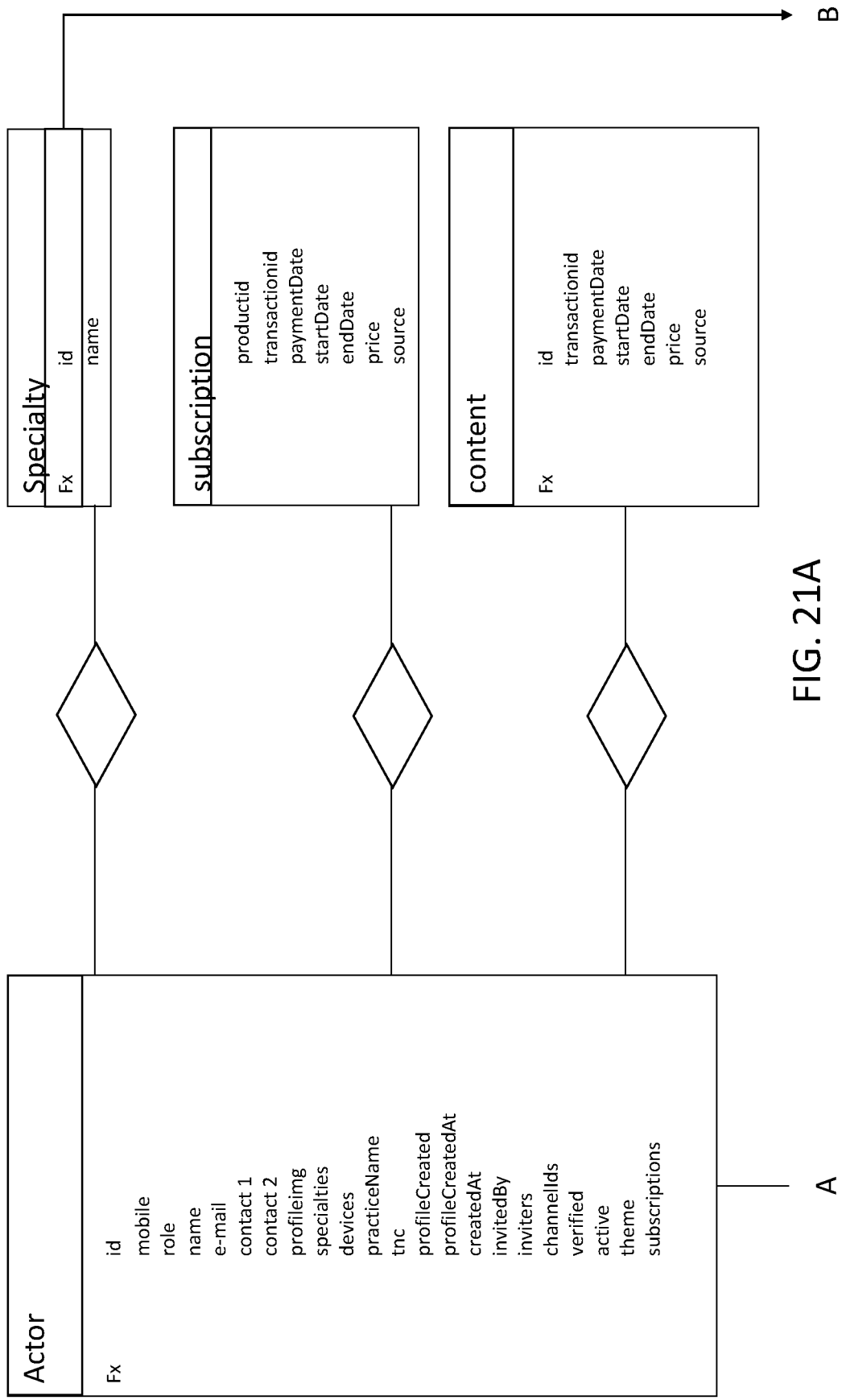
FIG. 21A is a database structure for the digital professional business card system.
Figure 21B:
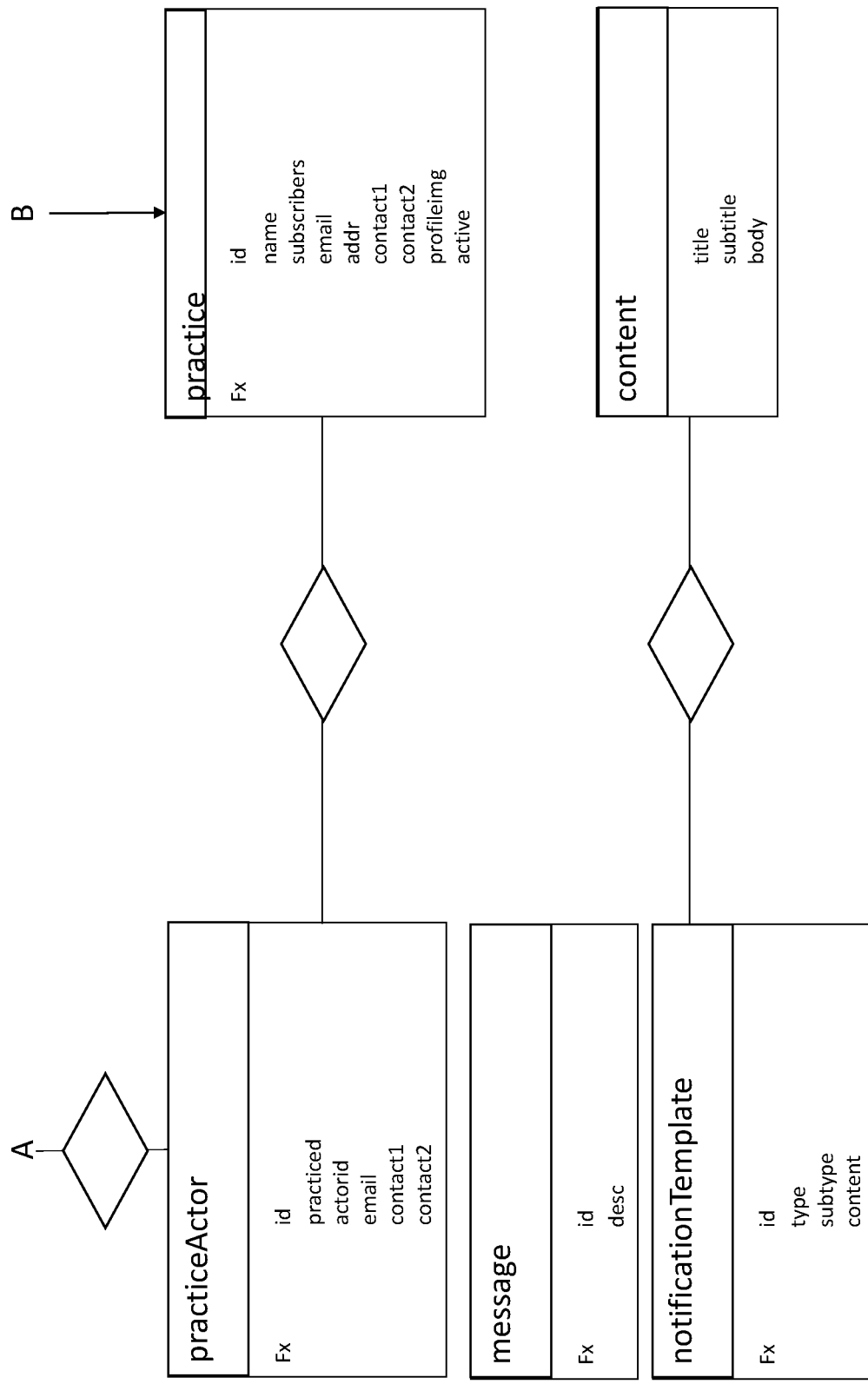
FIG. 21B is a continuation of the database structure for the digital professional business card system shown in FIG. 16A.

A representative database structure is shown in reference to FIGS. 21A and 21B. The database structure includes a plurality of tables for each of an actor; a specialty; a subscription; a content; a practiceActor; a practice; a subscriber. The database architecture has a plurality of master and transactional tables.

Master tables include:
1) message—Table is to save all the messages using in application.
2) content—Table is used to save various content based upon content type, subtype; and a content, and can save different versions of a content type.
3) Notification Template—Table is used to save various template/content for various types. Currently there are 2 types SMS and PUSH NOTIFICATION. In the SMS we have various sub types like SMS for digital card, SMS for invitation and SMS for OTP.
4) Specialty—The specialty table is used to save master specialties.

Transaction Tables include:
1. actor—The actor table is used to save all the users of application. The actor table also includes the specialties (for clinicians and physicians). This table also includes Terms & Conditions accepted by user.
2. actorInvitation—The actorInvitation table is used to save a practice's passcode, which will be used by Practice Administrator to register the practice.
3. practice—The practice table is used to save information pertaining to all practices. The practice table able also include specialties and subscribers (count and role).
4. practiceActor—The practiceActor table is used to save mapping between practice and actor. The practiceActor table retains the mapping of all clinicians invited by a practice and mapping of PA with practice.

As will be appreciated the system of the present invention is intended to provide a safe, secure, platform for digital messaging and sharing contact and business information. Within healthcare, this invention seeks to improve patient satisfaction and outcomes in healthcare and improve communication between different physicians, administrators, patients, and patient's families.

Using a smart phone, the present invention mitigates and prevents forgotten verbal communication and lost business cards. Establishing contact is instantaneous, requires minimum number of steps, and protects privacy (especially of the sender as their personal smartphone number is kept private). In addition, it establishes the basis for expanded two-way secure communication platform.

As described above, the application allows for the formation of group chats and allows for the electronic transfer of digital business cards. The invention digitizes and centralizes the way we communicate and share information with each other. Users can download, store and organize existing cards they have received within their interface and their portal and save these cards with them forever. The invention allows for the exchange of digital business cards through a cellular application with the sender's personal number remaining private. Users can share the business cards of colleagues as well through the application with other participants. Within healthcare, the application allows for direct and group messaging between various industry stakeholders (physician to physician, physician to patient) and allows users to search for other members in a centralized database with specific search queries. As such, knowing the personal and private cell phone number of key players within the industry is not needed. In this way, different members can communicate through the application without all parties knowing the personal cell phone number of different members.

Aspects of the present invention provide a paperless digital business card 20 that is based on a digital application 60. Two parties with smart phones, one of which would have the digital application 60 will provide a medium of communication that is reliable, reproducible, secure, and enhances a digital business environment. Although the digital business card 20 will revolutionize all business communications, its impact is more pronounced in some businesses like healthcare.

Continuing from our previous example, a specialist visiting a patient in the hospital takes the smart phone number of the patient and enters into his application. The application then sends a message to the patient's smart phone about the specialist's name, contact information, follow-on appointments, and even instructions about follow-on care. Close relatives can provide their smart phone numbers as well, if they want (or need) to be contacted by specialist with regard to their loved ones' care. Obtaining the patient's consent at the onset eliminates the need for follow up consent processes for the sharing of healthcare information.

Information is then sent automatically on daily or other temporally recurring basis about the progress of the patient's recovery. Results of any tests can also be sent through the "application" in an encrypted form between the parties involved. The one or more Healthcare providers can also organize the communication with patients, relatives, and other physicians in folders for better efficiency. All this information transmission will be secure and compliant with privacy and HIPAA regulations.

Although, this application is primarily intended for the healthcare industry, it is applicable in other businesses as well. It helps establish communication between two parties in a secure way, instantly. In another non-limiting example, a salesperson is manning a booth at a convention, which is attended by thousands of participants. When a few hundred participants visit that person's booth, some of them exchange business cards. A smaller percentage actually establish further communication later. However, the application can be used by the salesperson to instantly establish communication with an interested party right away by obtaining an office phone number or another personal phone number. The sales person enters the phone number into the application and both parties can start communicating, without lost business cards or forgotten information. The information can be transmitted not only between mobile devises, but also office networks. Different folders can be created within the app, which allows the user easy access to the content.

Thus, the digital business card 20 provides secure, reliable two-way communication, which can become active form by the action of either patient or healthcare provider, or between parties in a business relationship. With the digital business card application 60 and system providing communications through smart phone, there are no more lost business cards and forgotten verbal communication. Establishing contact is instantaneous and requires a minimum number of steps. In addition, it lays ground work for an expanded two-way secure communication platform.

Figures 16, 17:
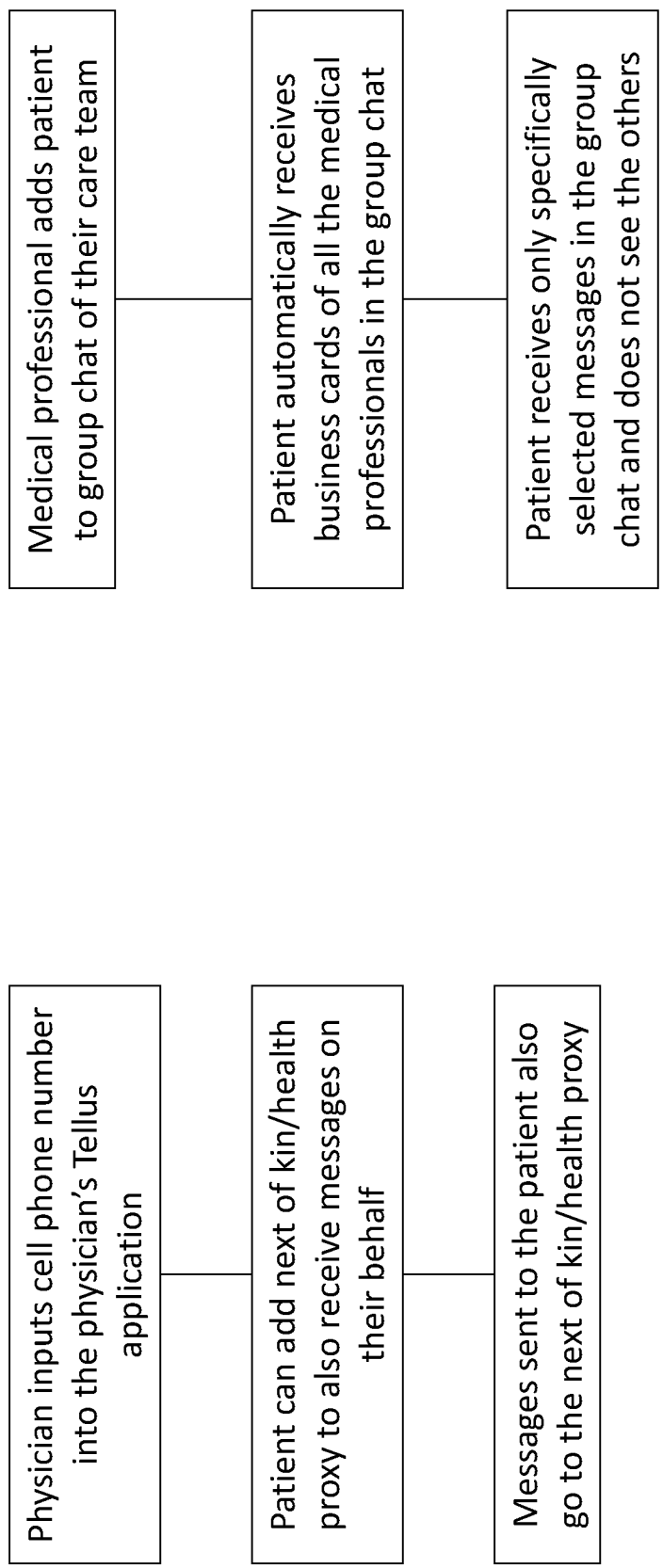
FIG. 16 is a flow chart for a patient providing a health proxy/next of kin identification to receive messages through the digital professional business card system.
FIG. 17 is a flow chart for sending a message to a care team and a patient through the digital professional business card system.
Figures 18, 19:
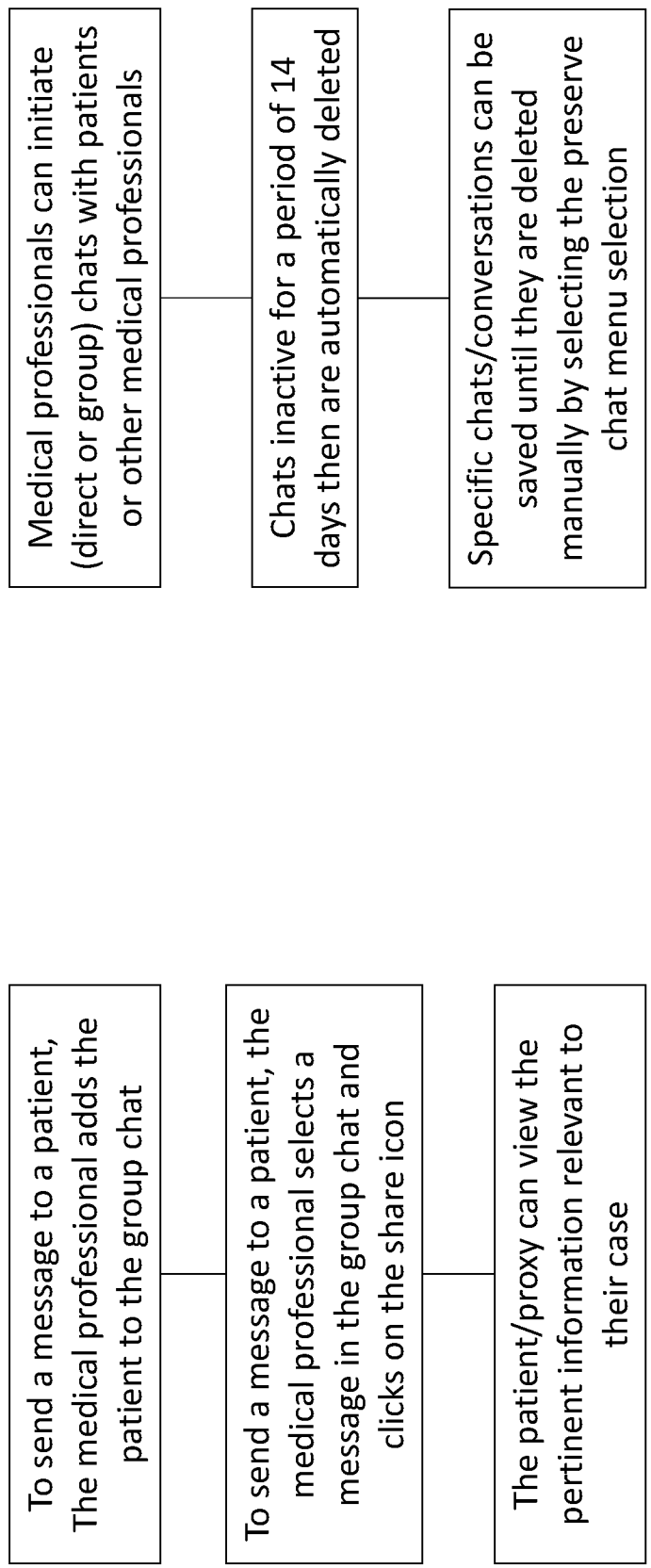
FIG. 18 is a flow chart for sending a message to a health proxy/next of kin through the digital professional business card system.
FIG. 19 is a flow chart for distributing contact information for members of a patient's care team through the digital professional business card system.
Figure 20:
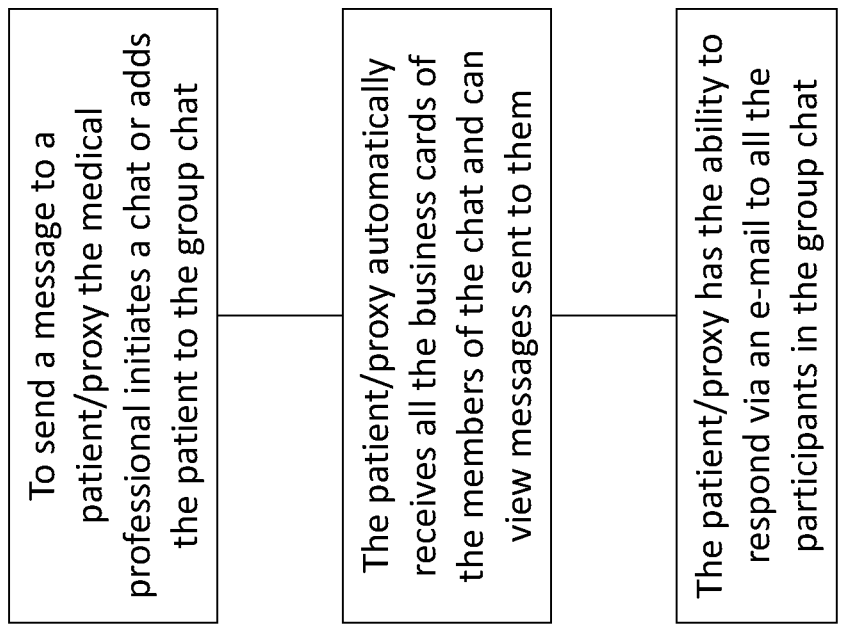
FIG. 20 is a flow chart for a messaging retention routine within the digital professional business card system.

In the use case shown in reference to FIG. 14, the Health care provider has smart phone 10 with digital application 60. The Health care provider meets a patient in the hospital setting. After making a consultation, the health care provider requests their patient's smart phone number and adds the number to the application 60 on his smart phone, such as shown in FIG. 2. The digital application 60 from the health care provider records the information and starts communicating with the smart phone of the patient via a messaging framework 50. Likewise, as seen in reference to FIG. 16, once authorized, healthcare proxies/next of kin smart phone numbers may be entered into the application 60. The same patient care information can be exchanged with them as well. Once the phone numbers are integrated into the health care provider's office digital network, information can be exchanged from office network as well. The same level of communication can be done through e mail as previously described.

In many instances a Health care specialist provider who sees a patient in the hospital setting may be unlikely to have prior contact and relationship with the patient. When the specialist is asked to provide specialty services, it would be the first time the patient has seen him/her as well. After a consultation is done, to provide continuity of care, the provider usually leaves his paper business card with the patient, or it is annotated on the patient's chart. In hospital setting, business cards get lost or misplaced. In addition, patient may not remember the names of multitude of specialists encountered. Care plan details may also forgotten. Follow up appointments after discharge from the hospital become cumbersome. By arranging contact between the smart phone of the patient and provider smart phone as well as the office network, all of the afore mentioned issues will be resolved.

The system of the present invention may include at least one computer with a user interface. The computer may include any computer including, but not limited to, a desktop, laptop, and smart device, such as, a tablet and smart phone. The computer includes a program product including a machine-readable program code for causing, when executed, the computer to perform steps. The program product may include software which may either be loaded onto the computer or accessed by the computer. The loaded software may include an application on a smart device. The software may be accessed by the computer using a web browser. The computer may access the software via the web browser using the internet, extranet, intranet, host server, internet cloud and the like.

The computer-based data processing system and method described above is for purposes of example only, and may be implemented in any type of computer system or programming or processing environment, or in a computer program, alone or in conjunction with hardware.

The present invention may also be implemented in software stored on a non-transitory computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the invention as set forth in the following claims.

What is claimed is:

1. A system for dissemination of a digital professional business card and communications between a patient care team of multiple professionals and a patient of the patient care team of the multiple professionals, comprising:
    a server configured to communicate with multiple computing devices;
    a messaging framework providing electronic communications between the multiple computing devices;
    a program product comprising machine-readable program code for causing, when executed, the server to perform process steps, comprising:
    receiving identification information for each of the multiple professionals for dissemination as the digital professional business card of each of the multiple professionals;
    receiving, from a first mobile computing device, a designation of the multiple professionals of the patient care team as a group chat for the exchange of communications concerning the patient; and
    transmitting the digital professional business card containing identification information for each of the multiple professionals of the patient care team to a second mobile computing device of the patient.

2. The system of claim 1, wherein the identification information includes a name, an occupation, a contact address, a phone number, and an image of the professional.

3. The system of claim 1, further comprising:
    responsive to an instruction received from the client, delivering the application to each of the multiple mobile computing devices.

4. The system of claim 1, further comprising:
    providing communications functionality between the the multiple computing devices.

5. The system of claim 4, wherein the communications functionality includes a chat messaging system.

6. The system of claim 5, wherein the chat messaging system receives a designation of a chat group from the first computing device, wherein the chat group includes the professional, the patient care team of professionals, and the patient.

7. The system of claim 6, wherein the chat messaging system receives an instruction from the first computing device to include the patient with a selected communication within the chat group.

8. The system of claim 6, further comprising:
delivering information corresponding to each member of the team of professionals to the second mobile computing device.

9. The system of claim 6, further comprising:
receiving a designation of a client proxy from the second computing device; and
transmitting chat group messages to a computing device of the client proxy.

10. The system of claim 5, further comprising:
receiving an instruction to preserve chat messages in a conversation from one or more of the first computing device and the second computing device; and
storing the chat messages in the conversation.

11. The system of claim 5, wherein the professional is a physician and the client is a patient.

12. A computer program product stored on a non-transitory computer storage medium comprising machine readable program code for causing, when executed, a computing device to perform process steps, comprising:
accessing a system, hosted on a server, for dissemination of a digital professional business card and a communication between multiple healthcare professionals on a patient care team and a patient treated by the patient care team;
receiving, from the server, a digital professional business card corresponding to each of the multiple healthcare professionals associated with the patient care team;
receiving, from the computing device, a designation of the multiple professionals of the patient care team as a participant in a group chat for the exchange of communications concerning the patient; and
transmitting the digital professional business card of each of the multiple professionals of the patient care team in the group chat to a second mobile computing device of the patient.

13. The computer program product of claim 12, further comprising:
receiving an input of the name and phone number of a client in an input field.

14. The computer program product of claim 13, further comprising:
transmitting an invitation comprising a V-card representation of the digital professional business card to the patient via an SMS message upon activation of the send button, the SMS message containing a link to access the computer program product.

15. The computer program product of claim 13, further comprising:
presenting a menu in the display, the menu providing a first control to initiate a chat messaging conversation and a second control designating a group to participate in a group chat messaging conversation.

16. The computer program product of claim 13, further comprising:
presenting a list of one or more conversations in the display, the list having a group icon for each of the one or more conversations corresponding to a group chat messaging conversation.

17. The computer program product of claim 16, further comprising:
an indicator on the group icon for designating the one or more group chat messaging conversations as restricting communication of the group chat messaging conversation with the patient.

18. The computer program product of claim 16, further comprising:
an indicator on the group icon showing that the chat messaging conversation is designated for preservation.

19. The computer program product of claim 17, further comprising:
presenting a conversation window displaying one or more chat communications for the group chat messaging conversation; and
presenting a representation of the group icon in the conversation window.

20. The computer program product of claim 19, further comprising:
presenting a conversation window displaying one or more chat communications for the group chat messaging conversation; and
presenting a representation of the group icon in the conversation window; and
when the group chat messaging conversation is designated as restricted, presenting a share control after each of the one or more chat communications in the group chat messaging conversation.

* * * * *